United States Patent
Choi et al.

(10) Patent No.: US 7,981,971 B2
(45) Date of Patent: *Jul. 19, 2011

(54) COMPOUNDING AGENT FOR RUBBER VULCANIZATION CONTAINING AMINO ALCOHOL SALT COMPOUND OF CARBOXYLIC ACID GROUP-CONTAINING DISULFIDE AND METHOD OF PRODUCTION OF THE SAME AND RUBBER COMPOSITION CONTAINING THE SAME

(75) Inventors: Wonmun Choi, Hiratsuka (JP); Takashi Kakubo, Hiratsuka (JP); Yuuki Shimizu, Hiratsuka (JP)

(73) Assignee: The Yokohama Rubber Co., Ltd., Tokyo (JP)

( * ) Notice: Subject to any disclaimer, the term of this patent is extended or adjusted under 35 U.S.C. 154(b) by 295 days.

This patent is subject to a terminal disclaimer.

(21) Appl. No.: 12/238,669

(22) Filed: Sep. 26, 2008

(65) Prior Publication Data

US 2009/0088532 A1    Apr. 2, 2009

(30) Foreign Application Priority Data

Sep. 28, 2007 (JP) ................................. 2007-255518
Sep. 28, 2007 (JP) ................................. 2007-255608

(51) Int. Cl.
*C08C 19/20* (2006.01)
*C07C 321/00* (2006.01)
*B32B 7/12* (2006.01)
*C08K 5/36* (2006.01)

(52) U.S. Cl. ......... 525/343; 562/432; 524/186; 524/303
(58) Field of Classification Search ............... 525/343; 562/432; 524/186, 303
See application file for complete search history.

(56) References Cited

U.S. PATENT DOCUMENTS 5,274,184 A * 12/1993 Nagl et al. ............... 562/429
7,714,049 B2 * 5/2010 Choi et al. ................. 524/186

OTHER PUBLICATIONS

A.V. Chapman, M. Porter, "Sulphur vulcanization Chemistry" in the Natural Rubber Science and Technology, Roberts, A.D. Ed., Oxford Science Publications, London, 1988.
Journal of SRIJ, vol. 65, p. 86, 1992.

* cited by examiner

*Primary Examiner* — William K Cheung
(74) *Attorney, Agent, or Firm* — Connolly Bove Lodge & Hutz LLP

(57) ABSTRACT

A compounding agent for rubber vulcanization containing an amino alcohol salt of a carboxylic acid group-containing disulfide, obtained by a reaction of a dithiocarboxylic acid and an amino alcohol, having the formula (i):

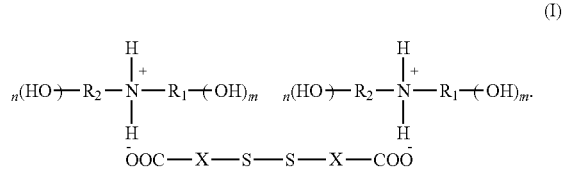

(I)

6 Claims, No Drawings

COMPOUNDING AGENT FOR RUBBER VULCANIZATION CONTAINING AMINO ALCOHOL SALT COMPOUND OF CARBOXYLIC ACID GROUP-CONTAINING DISULFIDE AND METHOD OF PRODUCTION OF THE SAME AND RUBBER COMPOSITION CONTAINING THE SAME

TECHNICAL FIELD

The present invention relates to a compounding agent for rubber vulcanization containing a novel amino alcohol salt of a carboxylic acid group-containing disulfide (hereinafter sometimes simply called an "amino alcohol salt of disulfide") and a method of production thereof and a rubber composition, in particular a rubber composition for metal bonding, containing the same.

BACKGROUND ART

In general, as a vulcanization accelerator for rubber, a thiuram-based, sulfenamide-based, mercaptobenzothiazole-based and other accelerators have been used. A sulfenamide-based accelerator is a delayed action accelerator. It is said that, during heating, the N—S bonds is dissociated by heat and mercaptobenzothiazole and amine are regenerated. It is known that the regenerated mercaptobenzothiazole acts as a vulcanization accelerator and the amine is coordinated to the zinc oxide and, therefore, plays an important role in accelerating the vulcanization reaction by activation of the vulcanization system and reaction with the vulcanization intermediates (see Chapman, A. V., Porter, M.: "Sulphur Vulcanization Chemistry" in the Natural Rubber Science and Technology, Roberts, A. D. Ed., Oxford Science Publications, London (1988)).

On the other hand, dibenzothiazole disulfide, which is a disulfide-based vulcanization agent, mercaptobenzothiazole is regenerated due to the dissociation of S—S bonds by heat but has no vulcanization activation capability due to amine, and, therefore, is said to be slow in accelerating vulcanization and inferior in vulcanization accelerating capability compared with sulfenamides. It may be considered to jointly use amines for the purpose of improving the vulcanization accelerating capability of dibenzothiazole disulfide, but in such a case there is the problem that, since free amines are high in reactivity, they react with the vulcanization agents such as sulfur even at a low temperature and have a detrimental effect on the scorch time.

The bonding performance between metal belts and rubber in pneumatic tires is, of course, important from the viewpoint of the fact that tires are composites. If this bonding performance is low, troubles such as tire separation are caused. As a countermeasure to this, the techniques of compounding of cobalt (Co) salts and the change of the vulcanization accelerator have been tried to make the bonding reaction dominant (see the Journal of SRIJ, vol. 65, p. 86 (1992)), but there are the problems of deterioration of the low heat buildup property.

DISCLOSURE OF THE INVENTION

Accordingly, objects of the present invention are to provide a compounding agent for rubber vulcanization containing an amino alcohol salt compound of a carboxylic acid group-containing disulfide capable of improving the vulcanization speed and the vulcanized rubber properties, without having a detrimental effect on the scorch time and the production method thereof and a rubber composition containing the same.

Another object of the present invention is to provide a rubber composition for metal bonding having an improved bonding performance with metal belts and a low heat buildup property suitable for use, for example, for rubber for a belt coat and/or belt edge cushion, etc. of a pneumatic tire.

In accordance with the present invention, there is provided a compounding agent for rubber vulcanization comprising an amino alcohol salt of a carboxylic acid group-containing disulfide having the formula (I):

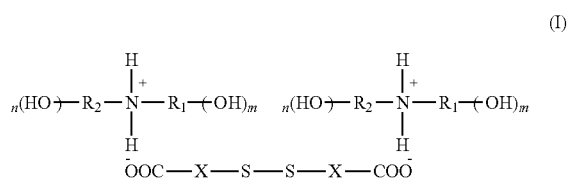

wherein $R_1$ and $R_2$ are, independently, hydrogen or a $C_1$ to $C_{20}$ organic group, which may have a hetero atom and/or a substituent group, $R_1$ and $R_2$ may bond together to form a ring, X indicates a $C_1$ to $C_{20}$ organic group, which may have a hetero atom and/or a substituent group, n and m are integers of 0, 1 or 2, and n+m is 1 to 4.

In accordance with the present invention, there is provided a compounding agent for rubber vulcanization comprising an amino alcohol salt compound of a carboxylic acid group-containing disulfide having the formula (I), wherein X is an aromatic group.

In accordance with the present invention, there is further provided a method for producing an amino alcohol salt compound of a carboxylic acid group-containing disulfide having the formula (I) obtained by reacting a disulfide compound having a carboxylic acid group having the formula (II) and an amino alcohol having the formula (III) (see following reaction formula (I)).

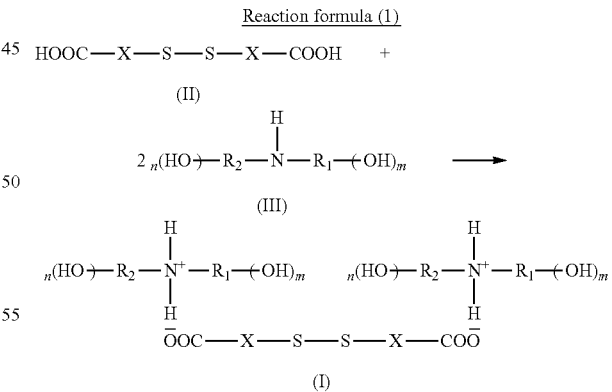

wherein $R_1$ and $R_2$ are, independently, hydrogen or a $C_1$ to $C_{20}$ organic group, which may have a hetero atom and/or a substituent group, $R_1$ and $R_2$ may bond together to form a ring, X indicates a $C_1$ to $C_{20}$ organic group, which may have a hetero atom and/or a substituent group, n and m are integers of 0, 1 or 2 and n+m is 1 to 4.

In accordance with the present invention, by using the amino alcohol salt of a disulfide compound having the formula (I), it is possible to give a high vulcanization acceleration effect to a diene-based rubber, halogenated butyl rubber, etc. and to improve the vulcanization speed and the vulcanized rubber properties (e.g., heat aging resistance or heat buildup property), without having a detrimental effect on the scorch time.

In accordance with the present invention, there is further provided a rubber composition for metal bonding containing (A) 100 parts by weight of a diene-based rubber, (B) 0.05 to 10 parts by weight of an amino alcohol salt compound of a carboxylic acid group-containing disulfide having the formula (I):

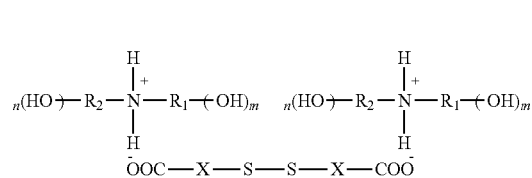

wherein $R_1$ and $R_2$ are, independently, hydrogen or a $C_1$ to $C_{20}$ organic group, which may have a hetero atom and/or a substituent group, $R_1$ and $R_2$ may bond together to form a ring, X indicates a $C_1$ to $C_{20}$ organic group, which may have a hetero atom and/or a substituent group, n and m are integers of 0, 1 or 2 and n+m is 1 to 4, obtained by a reaction of a dithiocarboxylic acid with an amino alcohol and (C) 0.05 to 5 parts by weight, in terms of a metal content, of an organic metal salt.

According to the present invention, by compounding an amine salt compound of a carboxylic acid-containing disulfide in the rubber composition, as a vulcanization accelerator, it is possible to achieve, for example, both an improvement in the bonding performance with the metal of a metal belt etc. and a low heat buildup property, of a pneumatic tire.

The inventors proceeded with research to solve this problem and, as a result, succeeded in enabling both the improvement of the bonding performance with the metal belt of a tire and a low heat buildup property by compounding blending an amine salt compound of a carboxylic acid-disulfide, as a vulcanization accelerator, into a rubber composition, together with the rubber component and organic metal salt.

BEST MODE FOR CARRYING OUT THE INVENTION

In this specification and in the claims which follow, the singular forms "a", "an" and "the" include plural referents unless the context clearly dictates otherwise.

The amino alcohol salt compound of a carboxylic acid group-containing disulfide according to the present invention (i.e., the amino alcohol salt of disulfide of the present invention) is a compound expressed by the formula (I).

In the formulae (I) to (III), $R_1$ and $R_2$ may independently be hydrogen or a $C_1$ to $C_{20}$, preferably $C_1$ to $C_{18}$ organic group, which may have a hetero atom and/or a substituent group. As such an organic group, for example, a methylene group, ethylene group, propylene group, butylene group, hexylene group, stearylene group, or other linear hydrocarbon groups, a cyclopropylene group, cyclobutylene group, cyclohexylene group, or other cyclic hydrocarbon groups, phenylene, naphthalene group, or other aromatic groups, etc. may be mentioned. The chains of these organic groups may have a nitrogen atom, oxygen atom, sulfur atom, or other hetero atoms.

As an example of such an organic group, for example, a methoxypropylene group, methoxyethylene group, etc. may be mentioned.

In the formula (I), X is an organic group selected from a $C_1$ to $C_{20}$, preferably $C_1$ to $C_{18}$, linear hydrocarbon group or alicyclic hydrocarbon group, aromatic hydrocarbon group, and heterocyclic group all of which may have a substituent group(s). As examples of this organic group, for example, a methylene group, ethylene group, propylene group, hexylene group, cyclobutylene group, cyclohexylene group, phenylene group, thiazole group, thiadiazole group, pyridilene group, naphthylene group, etc. may be mentioned. When X is a linear hydrocarbon group or alicyclic hydrocarbon group, X may have a hetero atom selected from the group of a nitrogen atom, oxygen atom and sulfur atom in the carbon chain and may have a methyl, ethyl, or other alkyl groups, a bromo, chloro or other halogen groups and an ether group, ester group or other substituent groups. X is preferably a $C_1$ to $C_{18}$ linear hydrocarbon group, aromatic group, heterocyclic group or other aromatic groups. An aromatic group is more preferable. If X is an aromatic group, since an aromatic carboxylic acid has a higher acidity than an aliphatic carboxylic acid, has a high salt-forming capability with an amine and produces a stable amine salt, it is believed that there would be less detrimental effects on the scorching, etc. at the time of mixing of the rubber composition and of low temperature processing.

As the amino alcohol having the formula (III), ethanol amine, 3-amino-1-propanol, 2-amino-1-propanol, 1-amino-2-propanol, 4-amino-1-butanol, 2-amino-1-butanol, 2-amino-2-methyl-1-propanol, 5-amino-1-pentanol, 2-amino-1-pentanol, 6-amino-2-methyl-2-heptanol, 1-amino-1-cycloheptane methanol, 2-aminocyclohexanol, 4-aminocyclohexanol, 1-aminomethyl-1-cyclohexanol, 2-(2-aminoethoxy)ethanol, 2-(methylamino)ethanol, 2-(ethylamino)ethanol, 2-(propylamino)ethanol, diethanol amine, diisopropanolamine, serinol, 2-amino-2-ethyl-1,3-propanol, 2-amino-2-methyl-1,3-propanol, 3-pyrrolidinol, 2-piperidine methanol, 2-piperidine ethanol, 3-hydroxypiperidine, 4-hydroxypiperidine, 4-aminophenetyl alcohol, 2-amino-m-cresol, 2-amino-o-cresol, 2-amino-p-cresol, 5-amino-2-methoxyphenol, 2-amino-4-chlorophenol, 4-amino-3-chlorophenol, 4-amino-2,5-dimethylphenol, tyramine, 2-amino-4-phenylphenol, 1-amino-2-napthanol, 4-amino-1-napthanol, 5-amino-1-napthanol and dopamine may be mentioned. Among these, 2-aminoethanol, 1-amino-2-propanol, 4-hydroxypiperidine, diisopropanolamine and diethanol amine are preferable due to their good industrial availability.

The amino alcohol salt of a disulfide compound (I) according to the present invention can be produced, as shown in the reaction formula (1), by reacting the disulfide compound having a carboxylic acid group shown in the formula (II), wherein X is as defined above, and the amino alcohol having the formula (III), wherein R is as defined above. This reaction does not require a catalyst, etc. and can be produced by mixing and reacting the compounds having the formula (II) and the formula (III) in a suitable solvent (e.g., methanol, ethanol, propanol or another aliphatic alcohol, diethyl ether, tetrahydrofuran and other ethers, acetone, 2-butanone, and other ketones, etc.)

In the reaction formula (1), the amino alcohol (III) is preferably reacted with the carboxylic acid group of the disulfide compound (II) in a stoichiometric excess amount (e.g., 1.01 to 1.15 equivalents).

In the reaction formula (1), as a specific example of a carboxylic acid group-containing disulfide compound (II)

used as a starting material, for example, dithiodiglycolic acid, dithiodipropionic acid, 4,4'-dithiobutyric acid, dithiosalicylic acid, dithiobis(2-nitrobenzoic acid), etc. may be mentioned.

The reaction temperature of the reaction is not particularly limited, but is preferably in range of 0° C. to 100° C. If less than 0° C., the reaction time becomes slow, while at a temperature of more than 100° C., an unpreferable by-product reaction is liable to occur. This reaction temperature is more preferably in the range of 20° C. to 70° C.

As specific examples of the vulcanization agent usable in the rubber vulcanization compounding agent according to the present invention, for example, sulfur, organic peroxide, quinone dioxime, metal oxide, alkylphenol-formaldehyde resin, etc. may be mentioned.

As the compounding agent for rubber vulcanization jointly usable with the amino alcohol salt of disulfide according to the present invention, a sulfenamide-based or thiuram-based vulcanization accelerator is preferable. By the use of a sulfenamide-based or thiuram-based vulcanization accelerator, it is possible to further accelerate the vulcanization of the rubber component and to further improve the physical properties of the vulcanized rubber obtained. As the sulfenamide-based vulcanization accelerator, for example, N-cyclohexyl-2-benzothiazolyl sulfenamide, N-t-butyl-2-benzothiazolyl sulfenamide, N-oxydiethylene-2-benzothiazolyl sulfenamide and N,N'-dicyclohexyl-2-benzothiazolyl sulfenamide may be mentioned. As the thiuram-based vulcanization accelerator, for example, tetrakis(2-ethylhexyl) thiuram disulfide, tetramethyl thiuram disulfide, tetraethyl thiuram disulfide, tetramethyl thiuram monosulfide, tetrabenzyl thiuram disulfide and dipentamethylene thiuram tetrasulfide may be mentioned.

The rubber composition of the present invention includes an unvulcanized rubber component selected from the group consisting of a diene-based rubber and halogenated rubber and an amino alcohol salt of disulfide (I) according to the present invention. As the unvulcanized rubber component, which the present rubber composition may include, one is selected from the group consisting of a diene-based rubbers and halogenated rubbers. As specific examples of diene-based rubbers, for example, natural rubber, butadiene rubber, isoprene rubber, chloroprene rubber, styrene-butadiene copolymer rubber, ethylene-propylene diene copolymer rubber, and acrylonitrile-butadiene copolymer rubber may be mentioned. Further, as specific examples of halogenated rubbers, for example brominated butyl rubber, chlorinated butyl rubber, or other halogenated butyl rubber, halides of an isobutylene-paramethylstyrene copolymer (e.g., bromides), chloroprene rubber, epichlorohydrin rubber, chlorosulfonated polyethylene, chlorinated polyethylene, maleic-acid modified chlorinated polyethylene, chlorinated acryl rubber, fluororubbers, epoxylated acryl rubber and acryl rubber obtained by copolymerization of halogen-based monomers may be mentioned.

In the rubber composition of the present invention, the amino alcohol salt of disulfide (I) according to present invention may be used, as a rubber vulcanization compounding agent, alone or together with a vulcanization agent or vulcanization accelerator generally used, as a vulcanization agent or vulcanization accelerator for unvulcanized rubbers in the art. The amino alcohol salt of disulfide (I) according to the present invention can be used in any ratio with respect to the total amount of the other vulcanization agent and/or vulcanization accelerator contained in the present rubber vulcanization compounding agent, so long as the vulcanization and/or vulcanization acceleration action of the amino alcohol salt having disulfide (I) are not adversely affected and an improvement of the desired vulcanization and/or vulcanization acceleration effect and heat aging resistance can be achieved. However, to achieve the desirable vulcanization and/or vulcanization acceleration effect, the amount is preferably 0.05 to 20 parts by weight, based upon 100 parts by weight of unvulcanized rubber component selected from the group consisting of a diene-based rubber and halogenated rubber. If the amount of the amino alcohol salt of disulfide (I) is in this range, a more advantageous effect such as the ability to obtain a practical strength and rubber elasticity can be obtained. Further, the vulcanization temperature is usually preferably 140° C. to 200° C.

The rubber composition of the present invention may contain, in addition to the vulcanization accelerator, various types of agents and additives usually compounded into rubber compositions such as carbon black, silica or other reinforcing agents, vulcanization or cross-linking agents, vulcanization or cross-linking acceleration agents, stearic acid, zinc oxide, magnesium oxide, and other vulcanization acceleration aids, various types of oils, an antioxidant, filler, paraffin oil or other softening agent, a plasticizer, antioxidant, etc. in the amounts generally used depending upon various types of applications by general compounding methods. This compounding may be obtained by kneading by a general use rubber kneader, for example, rolls, a Banbury mixer, a kneader, etc.

As specific examples of the diene-based rubber able to compounded into the rubber composition in the second aspect of the present invention, for example, natural rubber, butadiene rubber, isoprene rubber, chloroprene rubber, styrene-butadiene copolymer rubber, ethylene-propylene diene copolymer rubber, and acrylonitrile-butadiene copolymer rubber may be mentioned. Further, as specific examples of halogenated rubber, for example, brominated butyl rubber, chlorinated butyl rubber, or other halogenated butyl rubber, a halide (for example, bromide) of an isobutylene-paramethyl styrene copolymer, chloroprene rubber, epichlorohydrin rubber, chlorosulfonated polyethylene, chlorinated polyethylene, maleic-acid modified chlorinated polyethylene, chlorinated acryl rubber, fluororubber, epoxylated acryl rubber, and an acryl rubber obtained by copolymerization of halogen-based monomers may be mentioned.

The rubber component compounded into the rubber composition, as the ingredient (A), in the second aspect of the present invention may be any diene-based rubber including natural rubber as explained above, but preferably natural rubber (NR) and/or polyisoprene rubber (IR) is compounded into 100 parts by weight of the diene-based rubber in an amount of at least 30 parts by weight, preferably 40 to 90 parts by weight. If the compounding amount of NR and/or IR is too small, the strength is insufficient, and therefore, this is not preferred. As the other diene-based rubber usable in the present invention, any diene-based rubber able to be compounded into a tire use rubber composition may be used. Specifically, butadiene rubber, chloroprene rubber, styrene-butadiene copolymer rubber, ethylene-propylene-diene copolymer rubber, acrylonitrile-butadiene copolymer rubber, etc. may be mentioned.

According to the second aspect of the present invention, the amine salt compound of a carboxylic acid-containing disulfide of the general formula (I) is compounded by an amount, based upon 100 parts by weight of the diene-based rubber, of 0.05 to 10 parts by weight, preferably 0.2 to 2 parts by weight. If the compounding amount of this amine salt compound of a carboxylic acid-containing disulfide (I) is too small, the modulus and bonding strength are insufficient, and, therefore, this is not preferred, while conversely if too large, the elongation at break and the bond durability become insufficient, and therefore, this is also not preferred.

In the second aspect of the present invention, the amino alcohol salt compound of a carboxylic acid group-containing disulfide used as the ingredient (B) (i.e., the amino alcohol salt of disulfide of the present invention) is a compound expressed by the formula (I).

According to the second aspect of the present invention, a metal bonding use rubber composition using an amino alcohol salt compound of a carboxylic acid group-containing disulfide having the formula (I), wherein, X in the formula (I) is an aromatic group is preferable.

The amino alcohol salt of disulfide compound having the formula (I) used in the present invention can be produced by reacting a disulfide compound having a carboxylic acid group having the formula (II) and an amino alcohol having the formula (III) (see the reaction formula (I)).

The amino alcohol salt of a disulfide compound (I) usable as the component (B) in the second aspect of the present invention can be produced, as shown in the above reaction formula (1), by reacting a disulfide compound having a carboxylic acid shown in the formula (II), wherein X is as defined above, and an amino alcohol having the formula (III), wherein R is as defined above. This reaction does not require a catalyst etc. The salt can be produced by mixing and reacting the compounds having the formula (II) and the formula (III) in a suitable solvent (e.g., methanol, ethanol, propanol, or other aliphatic alcohol, diethyl ether, tetrahydrofuran, or other ether, acetone, 2-butanone, or other ketones).

In the reaction formula (1), the amino alcohol (III) is preferably reacted with the carboxylic acid group of the disulfide compound (II) in a stoichiometrically excess amount (e.g., 0.95 to 1.15 equivalents).

As specific examples of the carboxylic acid group-containing disulfide compound (II) usable as the starting material in the above reaction formula (1), for example, dithiodiglycolic acid, dithiodipropionic acid, 4,4'-dithiobutyric acid, dithiosalicylic acid, dithiobis(2-nitrobenzoic acid), etc. may be mentioned.

The reaction temperature of the reaction is not particularly limited, but is preferably in the range of 0° C. to 100° C. If the temperature is less than 0° C., the reaction time becomes slow, while at a temperature of more than 100° C., an unpreferable by-product reaction is liable to occur. This reaction temperature is more preferably 20° C. to 70° C. in range.

To the rubber composition of the second aspect of the present invention, as the ingredient (C), an organic metal salt is compounded in an amount, as metal in terms of a content, based upon 100 parts by weight of the rubber component (A), of 0.05 to 5 parts by weight, preferably 0.2 to 2 parts by weight. If the compounding amount is too small, the bonding performance with metal belts is insufficient, and therefore, this is not preferable, while conversely if too large, the fatigue resistance becomes insufficient, and, therefore, this is in turn insufficient. As the organic metal salt usable in the present invention, use of a nickel (Ni) or cobalt (Co) salt is preferable. Specifically, nickel acetonyl acetate made by Nihon Kagaku Sangyo (Ni content 20.04%), cobalt naphthenate made by Nikko Materials (Co content 10%), Manobond made by Rhodia (Co content 22%), cobalt (II) tris-acetylacetonate made by Nihon Kagaku Sangyo (Co content 16.54%), etc. may be used.

The rubber composition for metal bonding according to the second aspect of the present invention may contain, as a vulcanization agent, for example, sulfur, organic peroxide, quinone dioxime, metal oxide, and alkylphenol-formaldehyde resin, etc.

In the rubber composition for metal bonding according to the second aspect of the present invention, the rubber vulcanization compounding agent usable together with the amino alcohol salt of disulfide preferably, includes a sulfenamide-based or thiuram-based vulcanization accelerator. By using a sulfenamide-based or thiuram-based vulcanization accelerator, it is possible to further accelerate the vulcanization of the rubber component and, further, to improve the physical properties of the vulcanized rubber obtained. As sulfonamide-based vulcanization accelerators, for example N-cyclohexyl-2-benzothiazolyl sulfenamide, N-t-butyl-2-benzothiazolyl sulfenamide, N-oxydiethylene-2-benzothiazolyl sulfenamide, N,N'-dicyclohexyl-2-benzothiazolyl sulfenamide may be mentioned. As the thiuram-based vulcanization accelerator, for example tetrakis(2-ethylhexyl) thiuram disulfide, tetramethyl thiuram disulfide, tetraethyl thiuram disulfide, tetramethyl thiuram monosulfide, tetrabenzyl thiuram disulfide and dipentamethylene thiuram tetrasulfide may be mentioned.

In a metal bonding rubber composition according to the second aspect of the present invention, the amino alcohol salt of disulfide (I) in the present invention may be used as a rubber vulcanization compounding agent, alone or together with a vulcanization agent or vulcanization accelerator generally used as a vulcanization agent or vulcanization accelerator of unvulcanized rubber in the art. The amino alcohol salt of disulfide (I) of the present invention can be used, in any ratio with respect to the total amount of the other vulcanization agent and/or vulcanization accelerator included in the rubber vulcanization compounding agent so long as the vulcanization and/or vulcanization acceleration action of the amino alcohol salt of disulfide (I) are not adversely affected and able to achieve an improvement in the desired vulcanization and/or vulcanization acceleration effect and heat aging resistance. However, to achieve the desirable vulcanization and/or vulcanization acceleration effect, it is preferably 0.05 to 10 parts by weight, based upon 100 parts by weight of the unvulcanized rubber component selected from the group consisting of diene-based rubbers and halogenated rubbers as explained above. If the compounding amount of the amino alcohol salt of disulfide (I) is in this range, more advantageous effects such as the ability to realize a practical strength and rubber elasticity can be obtained. Further, the vulcanization temperature is preferably the usual 140° C. to 200° C.

The rubber composition for metal bonding of the second aspect of the present invention may contain, in addition to the components (A) to (C), various types of compounding agents and additives usually compounded into the rubber compositions, such as carbon black, silica, or another reinforcing agent, a silane coupling agent, a vulcanization or cross-linking agent, a vulcanization or cross-linking accelerator, stearic acid, zinc oxide, magnesium oxide, or another vulcanization acceleration aid, various types of oils, an antioxidant, filler, paraffin oil, or other softening agent, a plasticizer, antioxidant, etc. in the amounts generally used in accordance with various types of applications by a general compounding method. This compound may be obtained by kneading by a general use rubber kneader, for example, rolls, a Banbury mixer, a kneader, etc.

EXAMPLES

The present invention will now be explained in further detail with reference to the Examples and Comparative Examples shown below, but the technical range of the present invention is by no means limited to these Examples.

Preparation Example 1

Synthesis of Compound 1

Into 1000 g of isopropanol, 306.4 g (1 mole) of dithiosalicylic acid and 122.16 g (2 moles) of 2-aminoethanol were added and reacted at room temperature for 30 minutes. After the end of the reaction, the product was filtered and dried to obtain the white powder Compound 1 shown by the following formula in an amount of 410.2 g (yield 95.7%):

(Compound 1)

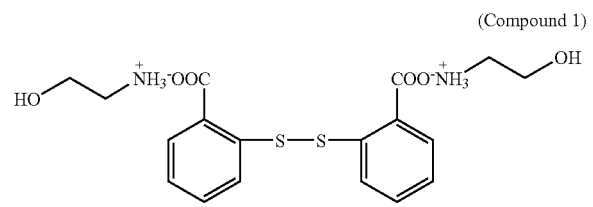

$^1$HNMR (400 MHz, DMSO-d6) δ in ppm: 2.9 (4H, CH$_2$—N), 3.6 (4H, CH—O), 7.1, 7.2, 7.5, 7.8 (8H, Ph)
Melting point (DSC): 147.4° C.

Preparation Example 2

Synthesis of Compound 2

Into 1000 g of isopropanol, 210.3 g (1 mole) of 3,3'-dithiodipropionic acid and 122.16 g (2 moles) of 2-aminoethanol were added and reacted at room temperature for 30 minutes. After the end of the reaction, the product was dried in vacuo to obtain the yellow powder Compound 2 shown by the following formula in an amount of 314.4 g (yield 94.5%).

(Compound 2)

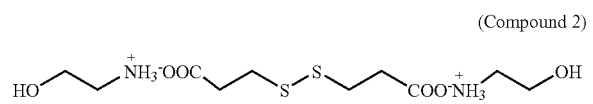

$^1$HNMR (400 MHz, D$_2$O-d2) δ in ppm: 2.3 (4H, CH$_2$—S), 2.8 (4H, CH$_2$—COO), 2.9 (4H, CH$_2$—N), 3.6 (4H, CH—O)

Preparation Example 3

Synthesis of Compound 3

Into 1000 g of isopropanol, 306.4 g (1 mole) of dithiosalicylic acid and 150.2 g (2 moles) of 1-amino-2-propanol were added. The result and product was reacted at room temperature for 30 minutes. After the end of the reaction, the product was filtered and dried to obtain the brown powder Compound 3 shown in the following formula in an amount of 410.2 g (yield 95.7%).

(Compound 3)

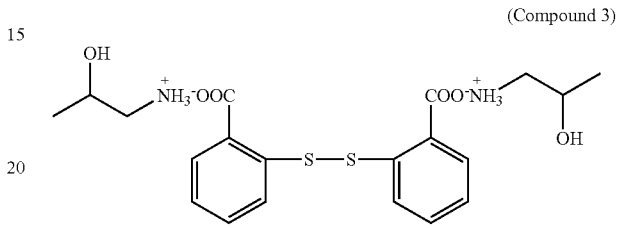

$^1$HNMR (400 MHz, DMSO-d6) δ in ppm: 1.1 (6H, CH$_3$), 2.8 (4H, CH$_2$—N), 3.9 (4H, CH—O), 7.1, 7.2, 7.5, 7.8 (8H, Ph)
Melting point (DSC): 176.2° C.

Examples 1 to 6 and Comparative Examples 1 to 3

Preparation of Rubber Composition

The ingredients of the formulations shown in the following Table I were mixed by a 1.7 liter Banbury mixer for 5 minutes to uniformly disperse them and obtain the rubber compositions of the Examples and Comparative Examples. The rubber compositions thus obtained of the Examples and Comparative Examples were evaluated by the following test methods. The results are shown in Table I.

TABLE I

| | Comp. Ex. 1 | Ex. 1 | Ex. 2 | Ex. 3 | Ex. 4 | Ex. 5 | Comp. Ex. 2 | Comp. Ex. 3 | Ex. 6 |
|---|---|---|---|---|---|---|---|---|---|
| Formulation (parts by weight) | | | | | | | | | |
| NR*[1] | 100 | 100 | 100 | 100 | 100 | 80 | 100 | — | — |
| SBR*[2] | — | — | — | — | — | 20 | — | — | — |
| Brominated butyl*[3] | — | — | — | — | — | — | — | 100 | 100 |
| Carbon black*[4] | 50 | 50 | 50 | 50 | 50 | 50 | 50 | 50 | 50 |
| ZnO*[5] | 3 | 3 | 3 | 3 | 3 | 3 | 3 | 3 | 3 |
| Stearic acid*[6] | 1 | 1 | 1 | 1 | 1 | 1 | 1 | 2 | 2 |
| Antioxidant*[7] | 1.5 | 1.5 | 1.5 | 1.5 | 1.5 | 1.5 | 1.5 | — | — |
| Petroleum resin*[8] | — | — | — | — | — | — | — | 10 | 10 |
| Oil*[9] | — | — | — | — | — | — | — | 10 | 10 |
| Sulfur*[10] | 1.5 | 1.5 | 1.5 | 1.5 | 1.5 | 1.5 | 1.5 | 0.5 | 0.5 |
| Compound 1*[11] | — | 0.5 | 1 | — | — | 1 | — | — | 2 |
| Compound 2*[11] | — | — | — | 1 | — | — | — | — | — |
| Compound 3*[11] | — | — | — | — | 1 | — | — | — | — |

TABLE I-continued

| | Comp. Ex. 1 | Ex. 1 | Ex. 2 | Ex. 3 | Ex. 4 | Ex. 5 | Comp. Ex. 2 | Comp. Ex. 3 | Ex. 6 |
|---|---|---|---|---|---|---|---|---|---|
| NS*[12] | 1.2 | 1.2 | 1.2 | 1.2 | 1.2 | 1.2 | 1.2 | — | — |
| DPG*[13] | — | — | — | — | — | — | 1 | — | — |
| DM*[14] | — | — | — | — | — | — | — | 1 | — |
| | | | | Evaluated properties | | | | | |
| Mooney scorch | | | | | | | | | |
| ML 5UP (min) | 16.8 | 16.5 | 15.9 | 15.4 | 16.2 | 17.0 | 9.7 | 16.3 | 16.7 |
| Rheometer | | | | | | | | | |
| T95 | 13.73 | 8.23 | 7.52 | 8.71 | 8.35 | 8.33 | 7.67 | 13.80 | 9.45 |
| Full automatic tension | | | | | | | | | |
| M100 | 2.6 | 2.8 | 3.0 | 2.9 | 3.0 | 2.9 | 3.1 | 0.8 | 1.3 |
| TB | 30.1 | 30.3 | 31.2 | 30.3 | 30.7 | 29.5 | 30.0 | 9.5 | 10.0 |
| EB | 500 | 499 | 492 | 493 | 501 | 501 | 479 | 832 | 785 |
| | | | Full automatic tension agin (100° C. × 48 hr) | | | | | | |
| M100 | 4.3 | 3.9 | 3.8 | 3.7 | 3.9 | 3.9 | 4.0 | 1.1 | 1.4 |
| TB | 26.5 | 28.5 | 27.9 | 27.6 | 28.7 | 28.3 | 27.3 | 9.1 | 9.9 |
| EB | 385 | 426 | 427 | 420 | 427 | 430 | 388 | 770 | 766 |

Table I notes
*[1]RSS#3
*[2]Nipol 1712 made by Nippon Zeon
*[3]Exxon Bromobutyl 2255 made by Japan Butyl
*[4]Diablack E made by Mitsubishi Chemical
*[5]Zinc Oxide No. 3 made by Seido Chemical Industry
*[6]Beads Stearic Acid YR made by NOF Corporation
*[7]Noccelar 6C made by Ouchi Shinko Chemical Industrial
*[8]Hilets G-100X made by Mitsui Chemicals
*[9]Desolex No. 3 made by Showa Shell Oil
*[10]Gold Flower band sulfur powder made by Tsurumi Chemical
*[11]See Preparation Examples 1 to 3
*[12]Noccelar NS-P made by Ouchi Shinko Chemical Industrial
*[13]Noccelar D made by Ouchi Shinko Chemical Industrial
*[14]Noccelar DM-P made by Ouchi Shinko Chemical Industrial Test Method Mooney Scorch The Mooney viscosity of unvulcanized rubber compositions were continuously determined according to the method of JIS K6300-1994 using an L-type rotor under the conditions of a preheating time of 1 minute and a test temperature of 125° C. The minimum value of the Mooney viscosity was made Vm. Further, the Mooney scorch time (min) was measured until the Mooney viscosity rose 5 points from Vm (ML 5UP). The results are shown in Table I. The Mooney scorch time is an indicator of scorching (rubber scorching). The longer the time, the result the better.

Rheometer

According to ASTM D2084, the vulcanization properties of the rubber composition of the present invention were determined at 150° C. (ASTM method for cross-linked rubber properties using oscillating disk cure meter). T95 shows the time until the cross-linking density becomes 95%, that is, the time until vulcanization is substantially completed.

Next, each rubber composition obtained was vulcanized at 150° C. for 30 minutes to prepare a 15 cm×15 cm×2 mm vulcanized sheet. From this vulcanized sheet, a JIS No. 3 dumbbell shaped test piece was punched out. According to JIS K6251, the modulus at 100% elongation (M100), the tensile strength at break at (TB) and the elongation at break (EB) were determined. Further, according to JIS K6257, M100, TB, and EB after aging at 100° C. for 48 hours were determined. The results are shown in Table I.

Examples 7 to 14 and Comparative Example 4

Preparation of Samples

In each of the formulations shown in Table II, the ingredients except for the vulcanization accelerator and sulfur were kneaded by a 1.7 liter internal mixer for 5 minutes. When reaching 160° C., the result art mixture was discharged to obtain a master batch. Into this master batch, the vulcanization accelerator and sulfur were kneaded by an open roll to obtain a rubber composition.

Next, each rubber composition obtained was vulcanized in a predetermined mold at 150° C. for 30 minutes to prepare a test sample which was then determined for the physical properties of the vulcanized rubber by the test methods shown below. The results are shown in Table II.

Physical Property Evaluation Test Methods

Strength at break: According to JIS K 6251, a dumbbell No. 3 type sample was drawn at a speed of 500 mm/min and the strength at break at 20° C. was determined. The results were shown, as indexed to the value of Comparative Example 4 as 100. The larger this value, the higher the strength.

Heat buildup: According to JIS K 6394, the tan δ at 60° C. was determined at an initial strain 10%, amplitude of 2%, and frequency of 20 Hz. The results are shown, as indexed to the value of Comparative Example 4 as 100. The smaller this value, the lower the heat buildup and the better the heat buildup property.

Unaged bonding performance test: Brass plated steel cords arranged in parallel at an interval of 12.7 mm were covered by the rubber composition, buried by a buried length of 12.7 mm, and bonded by vulcanization under vulcanization conditions of 160° C.×20 minutes to prepare a sample.

According to ASTM D-2229, the steel cords were pulled out from the sample. The amount of deposition of rubber covering the surface (%) was used for evaluation. The results are shown, as indexed to the value of Comparative Example 4 as 100. The larger this value, the more superior the bondability with rubber.

Aged bonding performance test: The vulcanized bonded sample was aged at a temperature of 70° C. and a humidity of 96% for 2 weeks. In the same way as the above unaged bondability, the amount of deposition of rubber covering the surface of the steel cord after being pulled out (%) was used for evaluation. The results are shown, as indexed to the value of Comparative Example 4 as 100. The larger this value, the more superior the bondability with rubber.

INDUSTRIAL APPLICABILITY

As explained above, the compounding agent for rubber vulcanization containing an amino alcohol salt of a disulfide compound (I) according to the present invention has a high vulcanization acceleration effect on a diene-based rubber, halogenated butyl rubber, etc. Further, compared with the compounding agent DPG used for improvement of the vulcanization acceleration ability, no detrimental effect on the scorch time, an indicator of a rubber composition, is exhibited. Furthermore, the vulcanized rubber obtained by vulcanizing an unvulcanized rubber composition containing a rubber vulcanization compounding agent containing an amino alcohol salt of a disulfide compound (I) according to the present invention exhibits a heat aging resistance higher than that obtained from an unvulcanized rubber composition containing a conventional vulcanization agent and/or vulcanization accelerator.

TABLE II

|   | Comp. Ex. 4 (Ref.) | Ex. 7 (Compound 1) | Ex. 8 (Compound 2) | Ex. 9 (Compound 3) | Ex. 10 (Cobalt salt 2) | Ex. 11 (IR) | Ex. 12 (SBR) | Ex. 13 (Small am't) | Ex. 14 (Large am't) |
|---|---|---|---|---|---|---|---|---|---|
| Formulation (parts by weight) | | | | | | | | | |
| NR*[1] | 100 | 100 | 100 | 100 | 100 | 80 | 90 | 100 | 100 |
| IR*[2] | — | — | — | — | — | 20 | — | — | — |
| SBR*[3] | — | — | — | — | — | — | 10 | — | — |
| CB*[4] | 60 | 60 | 60 | 60 | 60 | 60 | 60 | 60 | 60 |
| Zinc oxide*[5] | 8 | 8 | 8 | 8 | 8 | 8 | 8 | 8 | 8 |
| Stearic acid*[6] | 1 | 1 | 1 | 1 | 1 | 1 | 1 | 1 | 1 |
| Antioxidant 6PPD*[7] | 1 | 1 | 1 | 1 | 1 | 1 | 1 | 1 | 1 |
| Antioxidant RD*[8] | 1 | 1 | 1 | 1 | 1 | 1 | 1 | 1 | 1 |
| Cobalt salt 1*[9] | 1 | 1 | 1 | 1 | — | 1 | 1 | 1 | 1 |
| Cobalt salt 2*[10] | — | — | — | — | 2 | — | — | — | — |
| Sulfur*[11] | 8 | 8 | 8 | 8 | 8 | 8 | 8 | 8 | 8 |
| Vulcanization accelerator DZ*[12] | 1 | — | — | — | — | — | — | — | — |
| Vulcanization accelerator NS*[13] | — | 1 | 1 | 1 | 1 | 1 | 1 | 1 | 1 |
| Compound 1*[14] | — | 1 | — | — | 1 | 1 | 1 | 0.5 | 3.0 |
| Compound 2*[15] | — | — | 1 | — | — | — | — | — | — |
| Compound 3*[16] | — | — | — | 1 | — | — | — | — | — |
| Physical properties | | | | | | | | | |
| Strength at break (MPa) | 23 | 25 | 25 | 25 | 27 | 23 | 23 | 24 | 28 |
| Heat buildup index (%) | 100 | 90 | 92 | 93 | 94 | 91 | 96 | 91 | 96 |
| Bonding performance index (%) | 100 | 105 | 106 | 103 | 110 | 105 | 102 | 102 | 109 |
| Post-aging bonding performance index (%) | 100 | 237 | 188 | 172 | 205 | 217 | 178 | 157 | 242 |

Table I notes
*[1]Natural rubber (RSS#3)
*[2]Nipol IR2202 made by Nippon Zeon
*[3]Nipol 1502 made by Nippon Zeon
*[4]Carbon Black Seast KH made by Tokai Carbon (iodine adsorption 90 cm$^3$/100 g, DBP absorption 119 × 10$^{-5}$ m$^3$/kg)
*[5]Zinc Oxide No. 3 made by Seido Chemical Industry
*[6]Beads Stearic Acid made by NOF Corporation
*[7]Santoflex 6PPD made by Flexsys
*[8]Noccelar 224 made by Ouchi Shinko Chemical Industrial
*[9]Manobond (Co content 22%) made by Rhodia (chemical formula: $(C_9H_{19}C_6O)_3B$)
*[10]Cobalt naphthenate (Co content 10%) made by Nikko Kinzoku
*[11]Crystex HS OT 20 made of AkzoNobel
*[12]Noccelar DZ-G made by Ouchi Shinko Chemical Industrial
*[13]Noccelar DM-P0 made by Ouchi Shinko Chemical Industrial
*[14]Compound 1: Compound A synthesized by Preparation Example 1
*[15]Compound 2: Compound B synthesized by Preparation Example 2
*[16]Compound 3: Compound C synthesized by Preparation Example 3

In the present invention, by compounding an amine salt compound of a carboxylic acid-containing disulfide and a metal salt into a diene-based rubber, the improvement in the bonding performance with a metal and a low heat buildup property both become possible, and therefore the invention is useful as a metal bonding rubber composition for belt coat rubber and/or a belt edge cushion of a pneumatic tire.

The invention claimed is:

1. A rubber composition comprising 100 parts by weight of at least one unvulcanized rubber component selected from the group consisting of diene-based rubbers and halogenated rubbers and 0.05 to 10 parts by weight of a compounding agent for rubber vulcanization comprising an amino alcohol salt of a carboxylic acid group-containing disulfide having the formula (I):

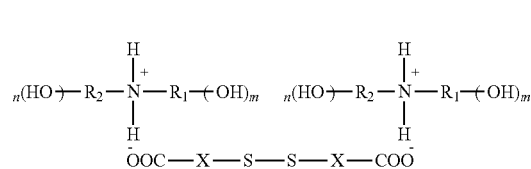

wherein $R_1$ and $R_2$ are, independently, hydrogen or a $C_1$ to $C_{20}$ organic group, which may have a hetero atom and/or a substituent group, $R_1$ and $R_2$ may bond together to form a ring, X indicates a $C_1$ to $C_{20}$ organic group, which may have a hetero atom and/or a substituent group, n and m are integers of 0, 1 or 2, and n+m is 1 to 4, which is obtained by a reaction of a dithiocarboxylic acid and an amino alcohol.

2. A rubber composition for metal bonding comprising (A) 100 parts by weight of a diene-based rubber, (B) 0.05 to 10 parts by weight of an amino alcohol salt compound of a carboxylic acid group-containing disulfide having the formula (I):

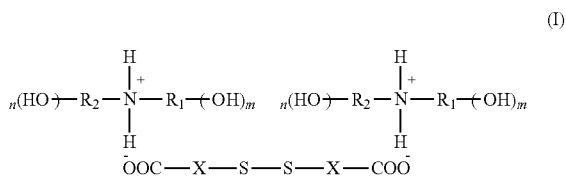

wherein $R_1$ and $R_2$ are, independently, hydrogen or a $C_1$ to $C_{20}$ organic group, which may have a hetero atom and/or a substituent group, $R_1$ and $R_2$ may bond together to form a ring, X indicates a $C_1$ to $C_{20}$ organic group, which may have a hetero atom and/or a substituent group, n and m are integers of 0, 1 or 2 and n+m is 1 to 4, which is obtained by a reaction of a dithiocarboxylic acid and an amino alcohol and (C) 0.05 to 5 parts by weight, in terms of a metal content, of an organic metal salt.

3. A rubber composition for metal bonding as claimed in claim 2, wherein X in the formula (I) is an aromatic group.

4. A rubber composition for metal bonding as claimed in claim 2, wherein the organic metal salt is an organic metal salt of nickel and/or cobalt.

5. A rubber composition as claimed in claim 1, wherein X in the formula (I) is an aromatic group.

6. A rubber composition for metal bonding as claimed in claim 3, wherein the organic metal salt is an organic metal salt of nickel and/or cobalt.

* * * * *